US00PP36704P2

(12) United States Plant Patent
Kerley

(10) Patent No.: US PP36,704 P2
(45) Date of Patent: May 20, 2025

(54) *NEMESIA* PLANT NAMED 'KERNEMBIRD'

(50) Latin Name: *Nemesia fruticans*
Varietal Denomination: KERNEMBIRD

(71) Applicant: Timothy Edward Kerley, Willingham (GB)

(72) Inventor: Timothy Edward Kerley, Willingham (GB)

(73) Assignee: Kerley & Co Ltd (GB)

( * ) Notice: Subject to any disclaimer, the term of this patent is extended or adjusted under 35 U.S.C. 154(b) by 0 days.

(21) Appl. No.: 18/753,874

(22) Filed: Jun. 25, 2024

Related U.S. Application Data

(60) Provisional application No. 63/621,683, filed on Jan. 17, 2024.

(51) Int. Cl.
*A01H 5/02* (2018.01)
*A01H 6/00* (2018.01)

(52) U.S. Cl.
USPC ..... Plt./458
CPC ..... *A01H 6/00* (2018.05)

(58) Field of Classification Search
USPC ..... Plt./458
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Nemesia fruticans* plant named 'KERNEMBIRD' is disclosed, characterized by bilabiate zygomorphic flowers with a nectar spur which flower acropetally towards the apex, giving a long flowering habit with no need to dead head. Flowers are medium blue in color and produce scant seed. Plants are compact and tolerant to both cold and heat. In commercial production the new variety is suitable for overwinter production cycles. The new variety is a *Nemesia*, normally used as an ornamental garden or container plant.

2 Drawing Sheets

Figure 1:
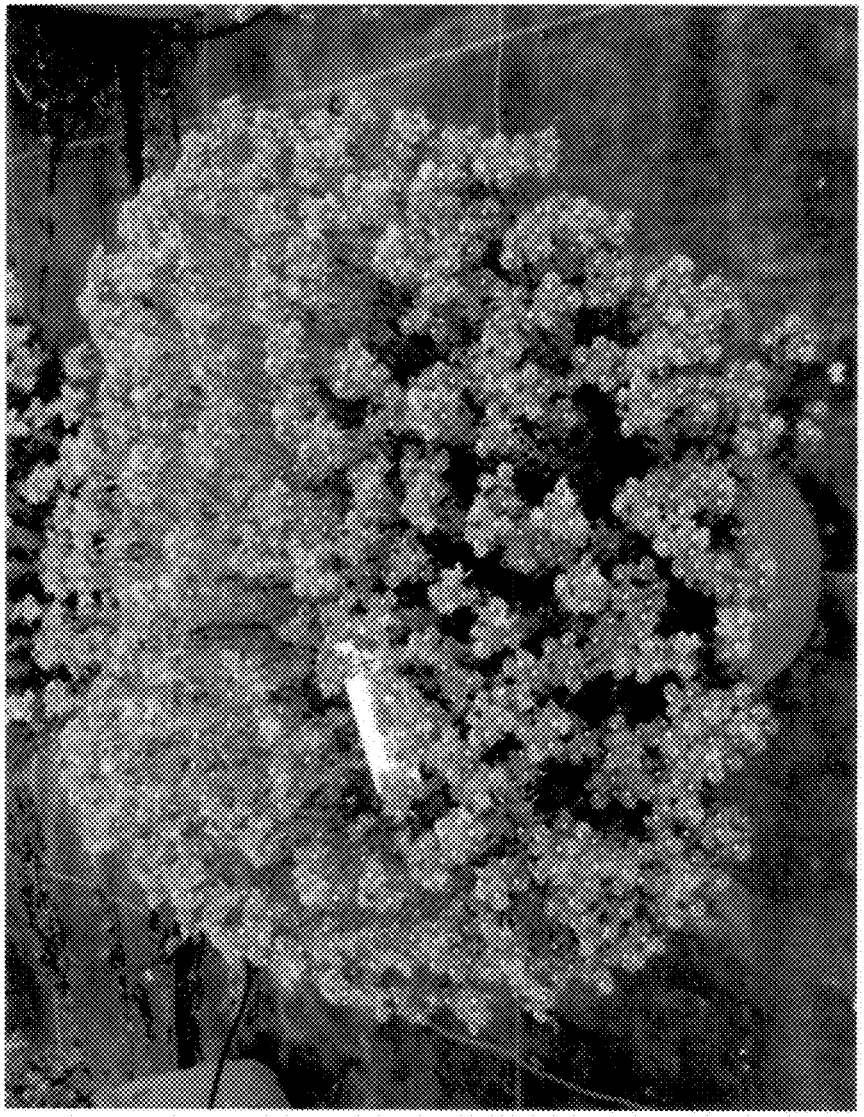

Latin name of the genus and species: *Nemesia fruticans*.
Cultivar denomination: 'KERNEMBIRD'.

BACKGROUND OF THE INVENTION

The new *Nemesia* cultivar is a product of a planned breeding program conducted by the inventor at a commercial greenhouse in Cambridge, United Kingdom. The objective of the breeding program was to produce new *Nemesia* varieties for ornamental commercial applications.

The seed parent is an unnamed, unpatented proprietary seedling *Nemesia fruticans*. The pollen parent is a different unnamed, unpatented proprietary cultivar *Nemesia fruticans*. The cross pollination resulting in this new cultivar was made during June of 2019. The new cultivar was found and selected during February of 2020.

Asexual reproduction of the new cultivar was performed at a research greenhouse in Cambridge, United Kingdom in March of 2020 by vegetative terminal cuttings. This and subsequent propagation and has shown that the unique features of this cultivar are stable and reproduced true to type in multiple successive generations.

SUMMARY OF THE INVENTION

The cultivar 'KERNEMBIRD' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERNEMBIRD' These characteristics in combination distinguish 'KERNEMBIRD' as a new and distinct *Nemesia* cultivar:

1. Compact plant habit.
2. Medium blue flower color.
3. Low seed set.
4. Cold and heat tolerant.
5. Suitability for overwinter production cycles.
6. Bilabiate zygomorphic flowers with a nectar spur which flower acropetally towards the apex, giving a long flowering habit with no need to dead head.

PARENT COMPARISON

Plants of the new cultivar 'KERNEMBIRD' are comparable to the seed parent cultivar in most horticultural characteristics; however, the new cultivar 'KERNEMBIRD' differs in the following:

1. The new cultivar produces less seed than the seed parent.
2. The new cultivar branches more freely than the seed parent.
3. Plants of the new cultivar are more compact than plants of the seed parent.

Plants of the new cultivar 'KERNEMBIRD' are comparable to the pollen parent cultivar in most horticultural characteristics; however, the new cultivar 'KERNEMBIRD' differs in the following:

1. The new cultivar produces less seed than the pollen parent.
2. The new cultivar produces a deeper blue flower than the pollen parent.

3. The new cultivar flowers more consistently during summer than the pollen parent.

COMMERCIAL COMPARISON

Plants of the new cultivar 'KERNEMBIRD' are comparable to the commercial cultivar *Nemesia* 'Hubbird', U.S. Plant Pat. No. 12,014. The two *Nemesia* varieties are similar in most horticultural characteristics; however, the new cultivar 'KERNEMBIRD' differs in the following:

1. Plants of the new cultivar are more compact than plants of 'Hubbird'.
2. The new cultivar flowers more consistently during summer than the 'Hubbird'.

Plants of the new cultivar 'KERNEMBIRD' are comparable to the commercial cultivar *Nemesia* 'Melody Lilac Blue', unpatented. The two *Nemesia* varieties are similar in most horticultural characteristics; however, the new cultivar 'KERNEMBIRD' differs in the following:

1. Plants of the new cultivar are more compact than plants of this comparator.
2. The new cultivar flowers earlier in the spring than this comparator.
3. The new cultivar produces less seed than this comparator.
4. Flowers of the new cultivar are medium blue; flowers of this comparator are lilac-blue.

BRIEF DESCRIPTION OF THE PHOTOGRAPHS

The accompanying photograph in FIG. 1 illustrates in full color a typical plant of 'Kernembird'. The plant is approximately 24 weeks old.

Figure 2:
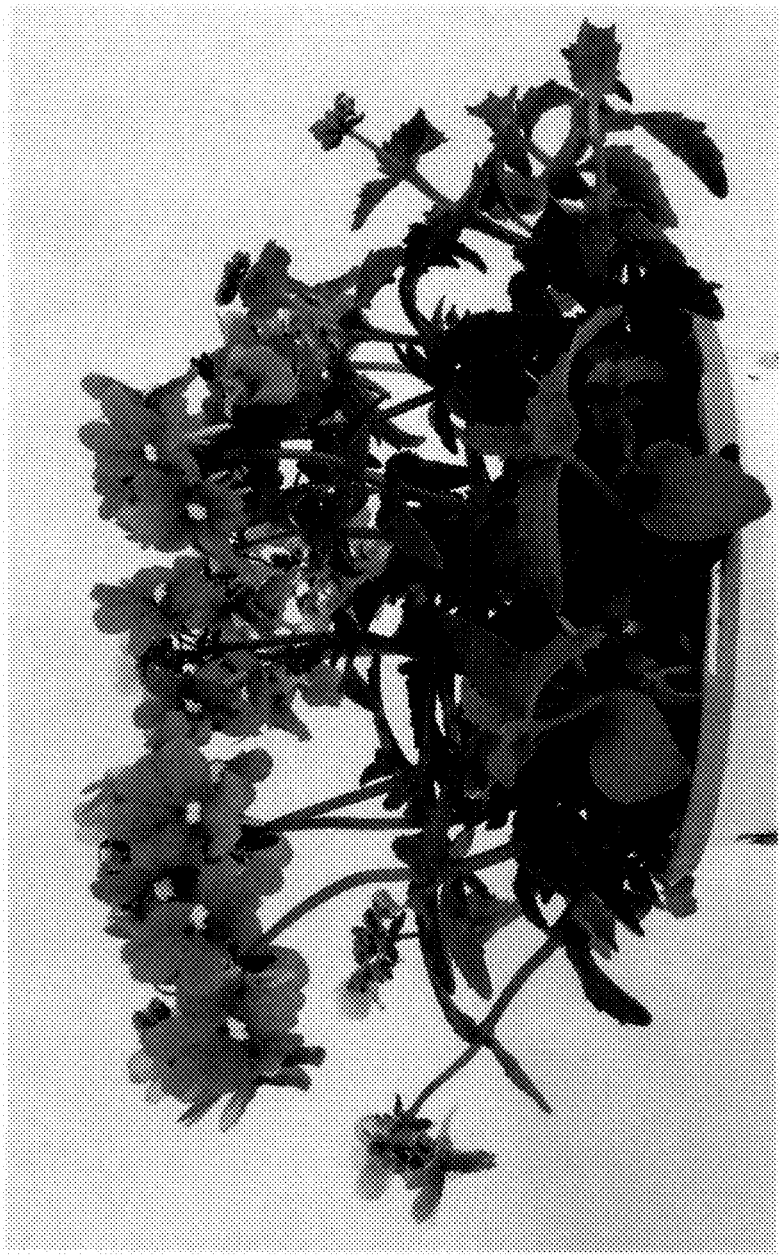

FIG. 2 illustrates a close-up view of the flowers and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'KERNEMBIRD' plants at about 6 months of age grown in a greenhouse in Cambridge, UK in a 2 liter pot. General light conditions are bright, normal sunlight. Measurements and numerical values represent averages of typical plant types.

Botanical classification: *Nemesia fruticans* 'KERNEMBIRD'.

PROPAGATION

Typical method: Terminal vegetative cuttings.
Time to initiate roots: About 7 days at approximately 18° C.
Time to produce a rooted liner: About 21 days at 18° C.

PLANT

Growth habit: Compact flowering perennial.
Pot size of plant described: 2 liter.
Height: Approximately 21 cm.
Plant spread: Approximately 28 cm.
Plant vigor: Vigorous.
Branching characteristics: Free-branching. Primary lateral branches with multiple secondary branches after pinching. Each branch growing a freely flowering terminal raceme.
Quantity of primary lateral branches: 5.
Quantity of secondary branches: 15.
Stem shape: Square in cross section with longitudinal ridges.
Branch length before peduncle: 15 cm.
Diameter: 4 mm.
Internode length: 3 cm.
Strength: Medium to strong.
Texture: Glabrous.
Color: RHS Yellow-Green 146B.
Root description: Fine, fibrous, colored near RHS White 155C.

FOLIAGE

Leaf:
*Arrangement.*—Decussate, single.
*Shape of blade.*—Lanceolate.
*Quantity per branch.*—*Average* 7.
*Attachment.*—Sessile, no petiole.
*Length.*—3.1 cm.
*Width.*—1.6 cm
*Apex.*—Narrowly acute.
*Base.*—Obtuse to rounded.
*Margin.*—Dentate.
*Texture of top surface.*—Smooth, glabrous.
*Texture of bottom surface.*—Smooth, glabrous.
*Stipule.*—None observed.
*Color.*—Young foliage upper side: RHS Yellow-Green 144A. Young foliage under side: RHS Yellow-Green 146B. Mature foliage upper side: RHS Green N137B. Mature foliage under side: RHS Yellow-Green 144A.
*Venation.*—Type: Pinnate. Venation color upper side: RHS Green N137D. Venation color under side: RHS Yellow-Green 144A.

FLOWER

Natural flowering season: March until October in Cambridge, UK.
Inflorescence type and habit: Terminal raceme. Zygomorphic flowers arranged acropetally from the base towards the apex facing up and out.
Individual flowers: Bilabiate with a nectar spur. Four upper petals are fused together at the base giving an arched, lobed banner lip. 2 central upper petals and 2 lateral upper petals. Lower lip is much larger with a nectar spur. Convex protuberance which is a landing platform for pollinators from which they can follow the path to the nectar.
Longevity of individual flowers: 20 to 22 days.
Fragrance: Faintly spice scented.
Inflorescence size:
*Length.*—5.5 cm.
*Width.*—5 cm.
Quantity of flowers per inflorescence: 12 open flowers and 12 buds present at one time.
Inflorescences per plant: Average range of 8 to 14 on a 6-month-old plant.
Flowers per plant: 190.

Corolla:
*Shape*.—Zygomorphic.
*Aspect*.—Upright to outward.
*Persistence*.—Self-cleaning.
*Size*.—2.3 cm high and 2.4 in diameter.
*Depth of flower with spur*.—2 cm.

Petals:
*Upper lateral petals*.—Shape: Obovate. Width: 8 mm. Length: 1.1 cm. Apex: Obtuse, rounded. Base: Fused to central petals. Margin: Entire, slightly undulating. Texture: Front: Glabrous. Back: Glabrous, matte. Color, mature: Front: RHS Violet 86C. Back: Near RHS Violet 86D. Color, when opening: Front: RHS Violet N81A. Back: RHS Purple 77B.
*Upper central petals*.—Shape: Spatulate. Width: 0.8 cm. Length: 1.2 cm. Apex: Obtuse, rounded. Base: Fused to lateral petals. Margin: Entire, slightly undulating. Texture: Front: Glabrous. Back: Glabrous, matte. Color, mature: Front: RHS Violet 86C. Back: RHS Violet 86D. Color, when opening: Front: RHS Violet N81A. Back: RHS Purple 77B.
*Lower petal*.—Shape: Broad obovate. Width: 1.9 cm. Length: 1.2 cm. Apex: Cordate. Base: Obtuse. Margin: Undulating, with slightly irregular dentations. Texture: Front: Glabrous. Back: Glabrous, matte. Color, mature: Front: RHS Violet 86B. Back: RHS Violet 86D. Color, when opening: Front: RHS Purple N81A. Back: RHS Purple 84A.
*Protuberance*.—Shape: Convex rectangular. Color: Near RHS Yellow 4A, changing to 7A at base. Length: 0.7 cm. Width: 0.4 cm. Texture: Slightly velvety.
*Throat*.—Diameter: 0.3 cm. Color: Upper throat: RHS Violet 92C. Lower throat: RHS Yellow 13B. Texture: Glabrous.
*Spur*.—Color: RHS Yellow-Green 149D. Diameter: 0.2 cm. Length: 0.8 cm. Shape: Narrow conical. Texture: Slightly pubescent.

Bud:
*Shape*.—Globular with a small spur.
*Color*.—Near RHS Greyed-Purple 186A, 186B and 186C (mixed).
*Size*.—4 mm in height and diameter.
*Texture*.—Glabrous.

Calyx: Star shaped, composed of 5 sepals fused at base.

Sepals:
*Shape*.—Elliptic.
*Apex*.—Acute.
*Base*.—Fused.
*Margin*.—Entire.
*Length*.—5 mm.
*Width*.—2 mm.
*Texture*.—Glabrous, upper and lower surfaces.
*Color*.—Upper surface: RHS Yellow-Green 146A. Lower surface: RHS Yellow-Green 146B.

Peduncle:
*Shape*.—Quadrate with prominent longitudinal veins.
*Length*.—10 cm.
*Diameter*.—3 mm.
*Strength*.—Medium.
*Texture*.—Glabrous. Slightly pubescent near flowers.
*Color*.—RHS Yellow-Green 146B.

Bracts: 1 at the base of pedicel on each flower.
*Shape*.—Ovate
*Length*.—5 mm.
*Diameter*.—2 mm.
*Apex*.—Rounded
*Texture*.—Upper: Glabrous. Lower: Pubescent.
*Color*.—RHS Green N137B.

Pedicel:
*Orientation*.—45° from peduncle.
*Texture*.—Pubescent.
*Length*.—About 16 mm.
*Diameter*.—2 mm.
*Color*.—RHS Yellow-Green 144B.
*Strength*.—Medium.

REPRODUCTIVE ORGANS

Androecium:
*Number of stamens*.—4 per flower curved around pistil and anthers in pairs.
*Filament*.—Pairs forming a heart shape around stigma.
*Filament length*.—About 9 mm.
*Anther shape*.—Basifixed.
*Anther length*.—About 6 mm.
*Color of pollen*.—RHS Yellow 13B.
*Pollen quantity*.—Moderate.

Gynoecium:
*Pistil number*.—1 per flower.
*Pistil length*.—0.2 cm.
*Style length*.—0.1 cm.
*Style color*.—RHS Yellow-Green 144D.
*Stigma shape*.—Globule.
*Stigma color*.—RHS Yellow-Green 144D.
*Ovary color*.—RHS Yellow-Green 144D.

OTHER CHARACTERISTICS

Seeds and fruits: Not observed.

Disease/pest resistance: Neither resistance nor susceptibility observed. Typical diseases include *Pythium* and *Phytopthera*. Various species of White Fly, Aphis and Mites may infect *Nemesia*.

Temperature tolerance: Observed tolerant of temperatures from −5° C. to 35° C. USDA Zones 9-10.

What is claimed is:

1. A new and distinct cultivar of *Nemesia* plant named 'KERNEMBIRD' as herein illustrated and described.

* * * * *